United States Patent
Yang

(10) Patent No.: US 7,670,049 B2
(45) Date of Patent: Mar. 2, 2010

(54) X-RAY RADIOGRAPHY APPARATUS AND ARRANGEMENT METHOD OF PLANE OF ROTATION

(75) Inventor: Xu Yang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 185 days.

(21) Appl. No.: 11/829,463

(22) Filed: Jul. 27, 2007

(65) Prior Publication Data

US 2008/0025473 A1    Jan. 31, 2008

(30) Foreign Application Priority Data

Jul. 28, 2006    (CN)    .................. 2006 1 0121405

(51) Int. Cl.
    *G01D 18/00*    (2006.01)
(52) U.S. Cl. .......................................... 378/207; 378/20
(58) Field of Classification Search ............... 378/4–20, 378/207, 97, 37, 205, 195, 208–209
    See application file for complete search history.

(56) References Cited

U.S. PATENT DOCUMENTS

| | | | |
|---|---|---|---|
| 3,700,894 A | 10/1972 | Counsell | |
| 4,907,251 A | 3/1990 | Mork et al. | |
| 5,717,735 A | 2/1998 | Ramsdell et al. | |
| 5,835,562 A | 11/1998 | Ramsdell et al. | |
| 7,110,494 B2 | 9/2006 | Groh et al. | |
| 7,212,608 B2 | 5/2007 | Nagamine et al. | |
| 7,212,609 B2 | 5/2007 | Nagamine et al. | |
| 2003/0043960 A1 * | 3/2003 | Op De Beek et al. | ......... 378/19 |

FOREIGN PATENT DOCUMENTS

JP    2001-346793    12/2001

* cited by examiner

*Primary Examiner*—Hoon Song
(74) *Attorney, Agent, or Firm*—Armstrong Teasdale LLP

(57) ABSTRACT

An adjustment method of a plane of rotation possesses has a step (S62) of detecting a range of the first X-rays from the X-ray tube 125 positioned at a first position with an X-ray detector 70; a step of moving the X-ray tube from the first the position to a second position; a step of detecting a range of the second X-rays from the X-ray tube positioned at the second the position with the X-ray detector 70; a step (S64) of calculating quantity of adjustment of the X-ray tube 125 and the collimator 126 based on the detected ranges by the first X-rays and the second X-rays.

18 Claims, 10 Drawing Sheets

A

B

C

X-RAY RADIOGRAPHY APPARATUS AND ARRANGEMENT METHOD OF PLANE OF ROTATION

CROSS REFERENCE TO RELATED APPLICATIONS

This application claims the benefit of Chinese Application No. 200610121405.6 filed Jul. 28, 2006.

BACKGROUND OF THE INVENTION

This invention relates to an X-ray radiography apparatus and the adjustment method of adjusting position between a X-ray tube and a collimator of an X-ray Computed Tomography (CT) system displaying a tomography images.

To acquire tomography image of each correct slice position of examinee's body in an X-ray radiography apparatus, for example, an X-ray CT system, examinee's body should be positioned precisely before a CT scan starts. Therefore whenever an X-ray tube is replaced and installed newly, a Plane of Rotation (POR), which is a plane formed by rotation of X-rays in a gantry, should be confirmed.

To confirm a plane of rotation, a phantom is placed on a cradle and a radiographic film is installed on the phantom. Then X-rays are irradiated through a collimator from the X-ray tube. After the radiographic film is exposed, the plane of rotation is identified based on the exposure state. Once the plane of rotation is comprehended, the correct slice position is identified by moving at least one of the X-ray tube and the collimator based on the result of the positional relation between the X-ray tube and the collimator. Related techniques hitherto proposed are disclosed for example in JP 2001-346793 A.

SUMMARY OF THE INVENTION

The above prior art has to spent time and suffer trouble because it has to develop the radiographic film attached to the phantom.

Therefore one of purposes of this invention is to a X-ray radiography apparatus device and the adjustment method of confirming and adjusting a plane of rotation with an X-ray detector, without using radiographic film.

In a first aspect of the present invention, there is provided an X-ray radiography apparatus comprising: an X-ray detector for the X-ray tube position inspection, which detects the X-rays through the collimator from the X-ray tube at two or more different distances respectively; calculation means for calculating quantity of position gap of the X-ray tube using the difference of respective X-ray detection position detected at two or more different distances; and adjusting means for adjusting quantity of position gap of the X-ray tube based on the quantity of position gap of the X-ray tube calculated by the calculation means.

The X-ray radiography apparatus consistent with the first aspect of the present invention can calculate quantity of position gap of the X-ray tube with the difference of respective X-ray detection position detected at two or more different distances. And it can adjust the X-ray tube based on the quantity of position gap of the X-ray tube. Therefore, the first aspect can reduce the adjusting time and measure accurately.

In a second aspect of the present invention, an X-ray radiography apparatus detects X-rays through the collimator from the X-ray tube at two or more different distances respectively by placing the X-ray tube 180 degrees opposite across the X-ray detector for the X-ray tube position inspection.

The X-ray radiography apparatus consistent with the second aspect of the present invention can ensure two or more different distances by placing the X-ray tube 180 degrees opposite across the X-ray detector for the X-ray tube position inspection.

In a third aspect of the present invention, an X-ray radiography apparatus detects X-rays through the collimator from the X-ray tube at two or more different distances respectively by moving the X-ray detector for the X-ray tube position inspection to the X-ray tube.

The X-ray radiography apparatus consistent with the third aspect of the present invention can ensure two or more different distances by moving the X-ray detector for the X-ray tube position inspection to the X-ray tube.

In a fourth aspect of the present invention, an X-ray radiography apparatus has an X-ray CT unit for obtaining a tomography images of an examinee's body, providing a first X-ray tube, a first X-ray detector, placed the first X-ray tube opposite, for detecting irradiated X-rays from the first X-ray tube, rotor means for rotating around the examinee's body with maintaining position relations among the first the X-ray tube and the first X-ray detector, and a collimator having an opening limiting an X-ray range irradiated to the first X-ray detector; an X-ray CR unit for obtaining radiographic images of the examinee's body, providing a second X-ray tube, and a second X-ray detector, placed the second X-ray tube opposite across the examinee's body, for detecting irradiated X-rays from the second X-ray tube. In addition, the X-ray tube which the position gap is adjusted to the first the X-ray tube; the X-ray detector for the X-ray tube position inspection is the second X-ray detector; and the adjusting means adjusts position gap of the plane of rotation by rotor means of the X-ray CT unit.

The X-ray radiography apparatus consistent with the fourth aspect of the present invention has the X-ray CT unit and the X-ray CR unit, and it can adjust a position gap of a plane of rotation of the first X-ray tube of the X-ray CT by the second X-ray detector of the X-ray CR unit. Without preparing another X-ray detector and using radiographic film, it can adjust the first X-ray tube of the X-ray CT unit.

In a fifth aspect of the present invention, the X-ray detector for X-ray tube position inspection of this invention is located inside a cradle laying the examinee's body.

According to the X-ray radiography apparatus consistent with the fifth aspect of the present invention, it can reduce a cost because an X-ray detector of the X-ray CR unit is used, without preparing a particularly X-ray detector.

In a sixth aspect of the present invention, there is provided an adjustment method for adjusting a position of a plane of rotation comprising steps of: detecting a range of the first X-rays from the X-ray tube positioned at a first position with an X-ray detector; moving the X-ray tube from the first the position to a second position which is different from the first position; detecting a range of the second X-rays from the X-ray tube positioned at the second the position with the X-ray detector; and calculating quantity of adjustment of the X-ray tube and the collimator based on the detected ranges by the first X-rays and the second X-rays.

The adjustment method consistent with the sixth aspect of the present invention can adjust a plane of rotation with an X-ray detector electrically, without using radiographic film. The method can reduce the time for adjusting the plane of rotation, In addition, prior art cannot measure a radiographic film accurately because it is difficult for human eyes to confirm an X-ray light quantity difference, but this method of the sixth aspect measures it accurately by electric measurement.

In a seventh aspect of the present invention, the first position and the second position are placed 180 degrees opposite across the X-rays detector in the adjustment method of the plane of rotation.

The adjustment method of the seventh aspect can process data with simple operation because the first position and the second position are placed 180 degrees opposite.

In an eighth aspect, the step of calculating quantity of adjustment for the adjustment method calculates the quantity of adjustment by calculating the detected range width only by the second X-rays.

The adjustment method consistent with the seventh aspect of the present invention can calculate the detected range width based on the boundary line between the overlapped range of a detected range by the first X-rays and a detected range by the second X-rays, and the detected range width only by the second X-ray, and can calculate the error or gap of a plane of rotation of the X-ray tube based on the other known distances. The error shall be deemed as a quantity of adjustment.

In a ninth aspect, there is provided an adjustment method for adjusting a position of a plane of rotation comprising steps of: positioning an X-ray detector at a third position in an X-ray irradiation direction from the X-ray tube; detecting a range of the third X-rays from the X-ray tube with an X-ray detector positioned at the third the position; moving the X-ray detector to a fourth position in an irradiation direction that is different from the third the position; detecting a range of the fourth X-rays from the X-ray tube with an X-ray detector positioned at the fourth the position; and calculating quantity of adjustment the X-ray tube and the collimator based on the detected ranges by the third X-rays and the fourth X-rays.

The adjustment method consistent with the ninth aspect of the present invention can adjust a plane of rotation with an X-ray detector electrically, without using radiographic film. At the time, the quantity of adjustment can be found without turning around the X-ray tube.

In a tenth aspect of the adjustment method of this invention, the X-ray detector is located inside a cradle laying the examinee's body.

The adjustment method for adjusting a position of a plane of rotation consistent with the third aspect of the present invention can reduce a cost, for example, an X-ray detector for the CR photography can be used instead of preparing a particularly X-ray detector.

In an eleventh aspect, the step of calculating quantity of adjustment for the adjustment method calculates the quantity of adjustment by calculating detected range width only by the fourth X-rays.

The adjustment method consistent with the eleventh aspect of the present invention can calculate a detected range width based on the boundary line between the overlapped range of a detected range by the third X-rays and a detected range by the fourth X-rays, and the detected range width only by the fourth X-ray, and can calculate the error or gap of a plane of rotation of the X-ray tube based on the other known distances. The error shall be deemed as a quantity of adjustment.

In an twelfth aspect of the adjustment method of this invention, the method further comprising a step of moving the X-ray tube based on the quantity of the adjustment.

The adjustment method consistent with the twelfth aspect of the present invention can move the X-ray tube, and can position the plane of rotation to the center of the collimator.

In an thirteenth aspect of the adjustment method of this invention, the adjustment method of the plane of rotation is performed when the X-ray tube is installed first or when the X-ray tube is replaced.

The adjustment method consistent with the thirteenth aspect of the present invention can reduce a cost of changing X-ray tubes, because of adjusting a plane of rotation easily in a short time whenever the X-ray tube is replaced.

According to the X-ray radiography apparatus of this invention or the adjustment method of the plane of rotation, this invention adjusts a plane of rotation with an X-ray detector electrically, without using radiographic film. Therefore the development of radiographic film is not required and this invention can find quantity of adjustment automatically.

BRIEF DESCRIPTION OF THE DRAWINGS

The above aspects, other advantages and further features of the present invention will become readily apparent from the following description of illustrative, non-limiting embodiments with reference to accompanying drawings, in which:

FIG. 4A is a figure irradiating X-rays from the X-ray tube 125 positioned at a position of 0 degrees, and FIG. 4B a figure irradiating X-rays from the X-ray tube 125 positioned at a position of 180 degrees.

DETAILED DESCRIPTION OF THE EXEMPLARY EMBODIMENTS

<General Arrangement of X-ray Hybrid Diagnosis System>

Figure 1:
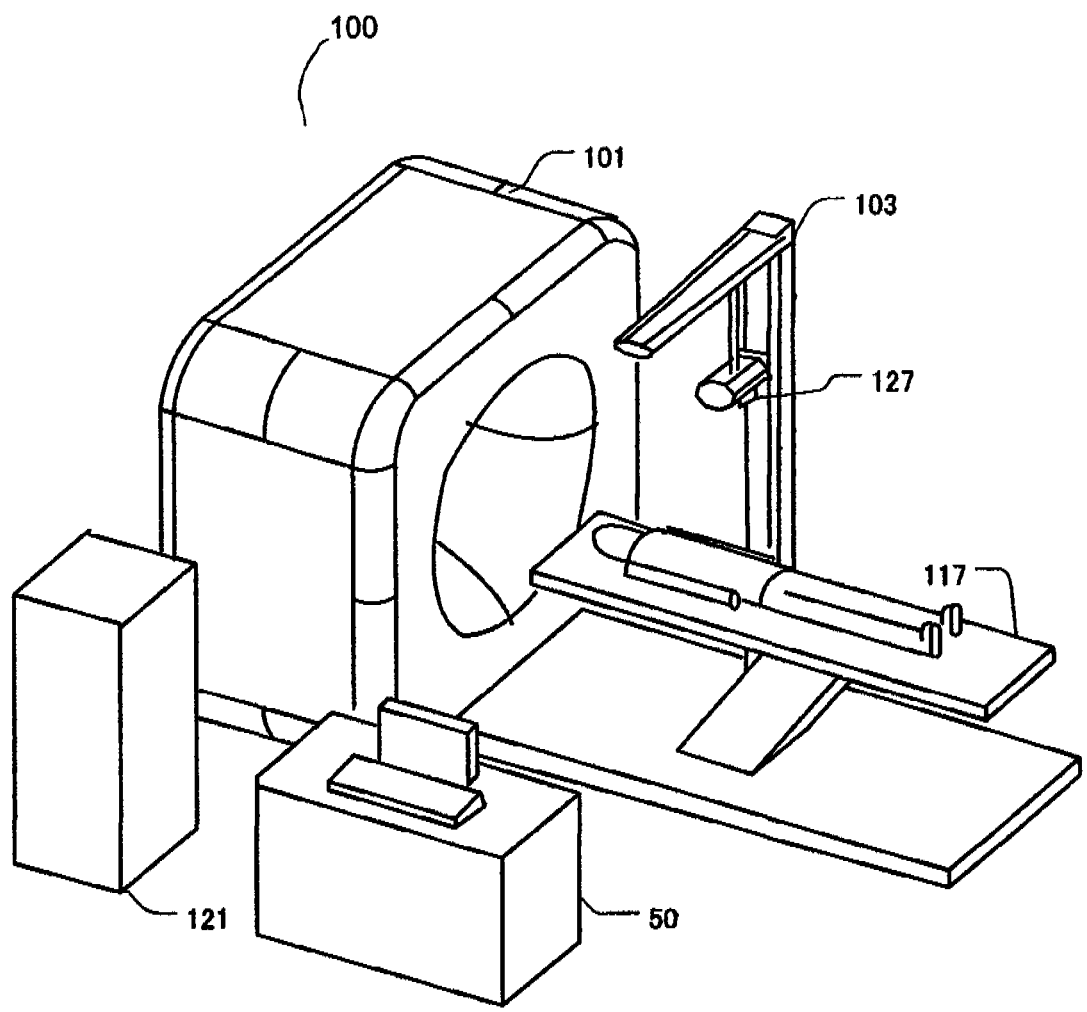
FIG. 1 is a perspective view showing a setup of an X-ray hybrid diagnosis system 100.
Figure 2:
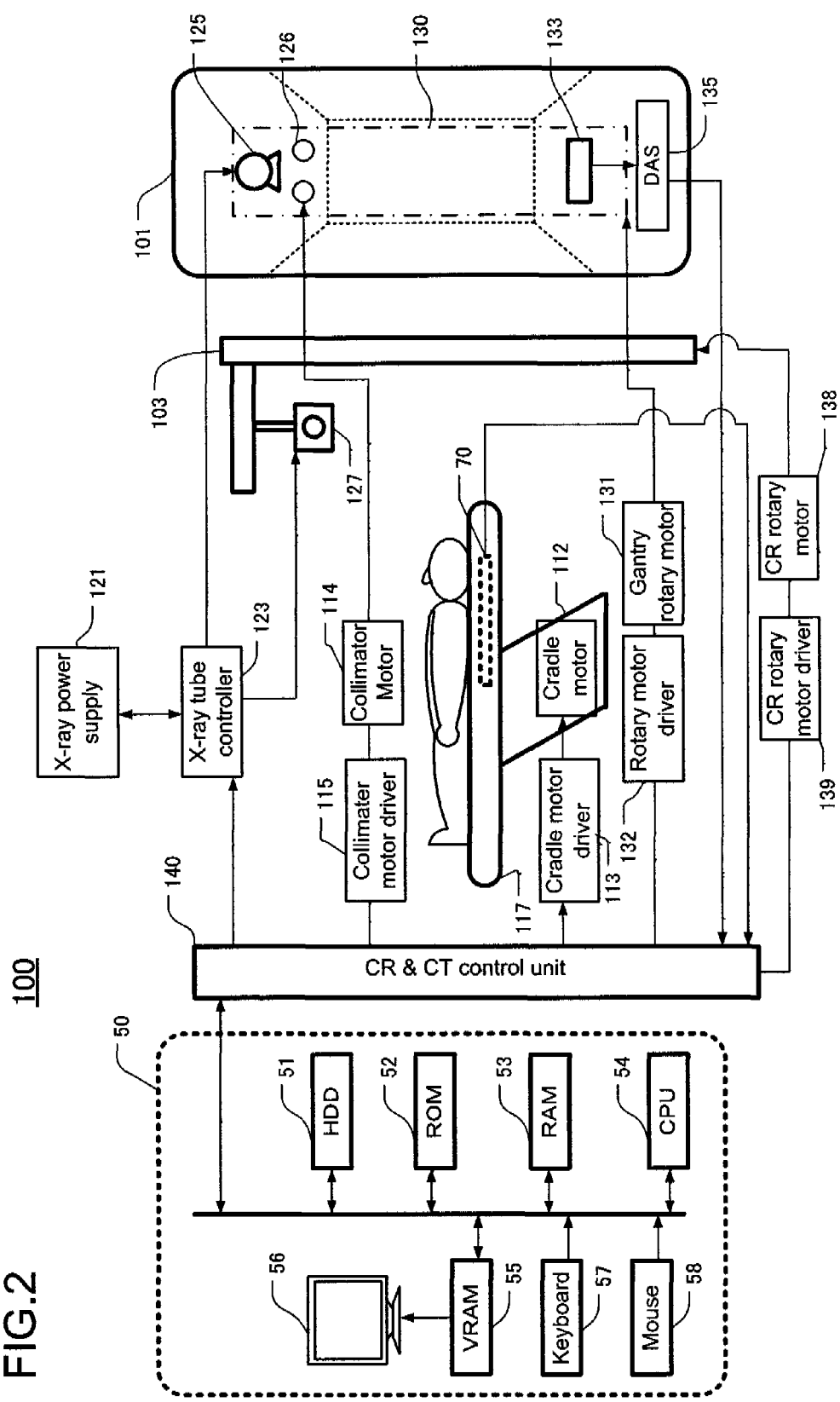
FIG. 2 is a block diagram representing the X-ray hybrid diagnosis system 100.

FIG. 1 is a perspective view showing a general arrangement of an X-ray hybrid diagnosis system 100 according to a first exemplary embodiment of the present invention. FIG. 2 is a block diagram representing an arrangement of the X-ray hybrid diagnosis system 100 according to one exemplified embodiment of the present invention. This system generally includes an operation console 50, a gantry 101, an X-ray power supply 121, and a CR unit 103. The gantry 101 is a computed tomography or CT unit adapted to acquire X-ray projection data to obtain tomography images of an examinee's body. The CR unit 103 is a computed radiography unit (digital X-ray imager) adapted to obtain X-ray radiographic images of the examinee's body. The operation console 50 is adapted to reconstruct an X-ray tomography image of an examinee's body based upon data transmitted from the gantry 101 and to display the X-ray tomography image. The operation console 50 is also adapted to display an X-ray radiographic image based upon data transmitted from a flat panel detector (denoted by 70 in FIG. 2). The cradle 117 is movable, with an examinee's body laid thereon in a decubitus position; The CR unit 103 is disposed at one side of the cradle 117.

The gantry 101 and the CR unit 103 are communicatively coupled with a CR & CT control unit 140 and various other devices which will be described later, and are configured to operate under control of the CR & CT control unit 140.

Inside the gantry 101 are provided an X-ray tube 125 for producing X rays, an X-ray tube controller 123 connected with the X-ray tube 125, a the collimator 126 for limiting a range of irradiation of X rays, a control motor 114 connected with the collimator 126 for regulating a dimension of an opening (slit or aperture) of the collimator, and a collimator driver 115. X rays that have passed through the collimator 126 form a fan-shaped beam (so-called "fan beam") of X rays.

Also provided inside the gantry 101 is an X-ray detection unit 133, which includes multiple rows of detection channels each having a plurality of detectors. Each detector has a length depending upon a fan angle (normally 60° or so). The detection channels are arranged in a direction (element direction) along the Z-axis direction. The X-ray detection unit 133 is, for example, made up of a scintillator and a photodiode used in combination.

The gantry 101 includes at least one data acquisition unit or DAS (standing for Data Acquisition System) 135 which acquires projection data from outputs of the detection channels. The number of the data acquisition unit(s) 135 may be one or more (e.g., four, eight, sixteen or thirty two), and each data acquisition unit 135 is connected with the X-ray detection unit 133. For example, the gantry 101 including four data acquisition units 135, which is normally called "4DAS", includes the detection channels arranged in four rows in the element direction, and can obtain four slice images in one cycle of revolution of the X-ray tube 125. The X-ray tube 125 and the X-ray detection unit 133 are disposed in opposite positions in the gantry 101 such that a hollow space for accommodating an examinee's body is left between the X-ray tube 125 and the X-ray detection unit 133. The X-ray tube 125 and the X-ray detection unit 133 are attached to a gantry rotor 130 so that the X-ray tube 125 and the X-ray detection unit 133 revolve around the examinee's body while maintaining the opposed positions relative to each other. A gantry rotary motor 131 and a gantry rotary motor driver 132 are connected with the gantry rotor 130, and the gantry rotor 130 is regulated by the gantry rotary motor driver 132 to make one rotation in about 0.3 second to about 1.0 second.

The CR unit 103 includes an X-ray tube 127 for producing X rays and a the collimator 126 having an opening for limiting a range of irradiation of X rays produced in the X-ray tube 127. The X-ray tube controller 123 is connected with the X-ray tube 127. Also provided in the CR unit 103 is a flat panel detector 70 adapted to receive X-rays from the X-ray tube 127.

The position of the X-ray tube 127 and the flat panel detector 70 can be adjusted through six degrees of freedom, in accordance with the posture (standing, sitting or decubitus position) of the examinee's body or the portion to be radiographed of the examinee's body. For that purpose, a CR rotary motor 138 and a CR rotary motor driver 139 are connected with the CR unit 103.

The cradle 107 is moved in the body-axial direction of the examinee's body (i.e., Z-axis direction) by a cradle motor 112. The cradle motor 112 is actuated by a cradle motor driver 113.

The CT & CR control unit 140 is communicatively coupled with the operation console 50. Responsive to instructions from the operation console 50, various control signals are transmitted to the X-ray tube controller 123, the cradle motor driver 113 and the rotary motor driver 132 as well as collimator driver 115 and the like. Data acquired by the data acquisition unit 135 are transmitted to the operation console 50 in which images are reconstructed and tomography images are displayed. Similarly, data obtained by the flat panel detector 70 are transmitted to the operation console 50 in which radiographic images are displayed.

The operation console 50 is typically embodied in a workstation, as illustrated in FIG. 2, which mainly includes a ROM 52 storing a boot program and the like, a RAM 53 serving as a main memory and a CPU 54 executing instructions for controlling the entire system.

A hard disk drive or HDD 51 is provided in the operation console 50 to store not only an operating system but also image-processing programs for providing various instructions given to the gantry 101 and the CR unit 103 and instructions to display radiographic images based upon data received from the flat panel detector 70, as well as image-processing programs for reconstructing and displaying X-ray tomography images based upon data received from the data acquisition unit 135. A VRAM 55 is a memory in which image data to be displayed are deployed, that is, the image data, etc. can be deployed in the VRAM 55 and thereby displayed in a monitor 56. Operators use a keyboard 57 and a mouse 58 to perform a variety of operations and manipulations.

<Cradle Structure>

Figure 3:
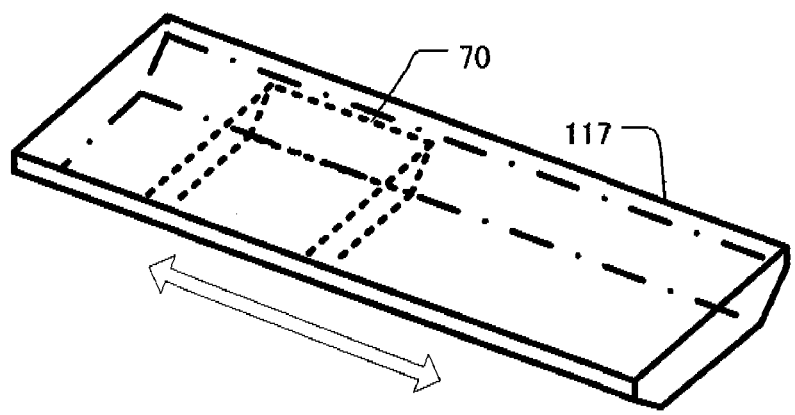
FIGS. 3A, 3B, and 3C show a structure of a cradle 117 in which a flat panel detector 70 is incorporated inside.
Figure 3:
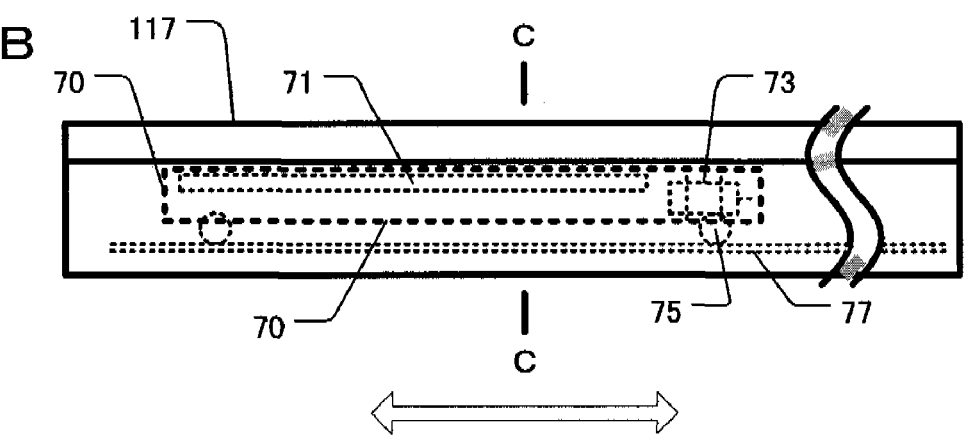
Figure 3:
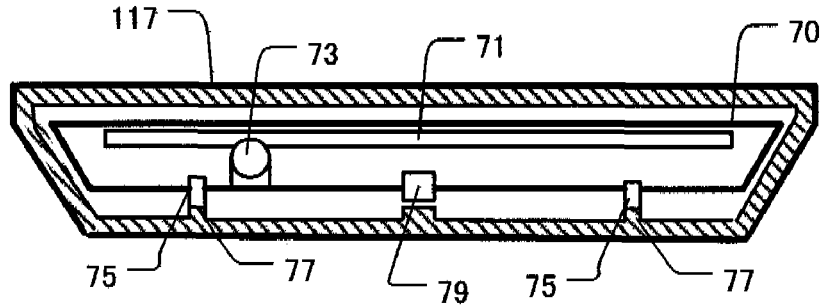

FIGS. 3A through 3C show a structure of the cradle 117. FIG. 3A is a perspective view of the cradle 117. FIG. 3B is a phantom showing the cradle 117 in cross section. FIG. 3C is a tomography view taken along line C-C of FIG. 3B. As shown in FIG. 3A, the cradle 117 has a hollow space and made of X-ray transparent material such as plastic. In this hollow space is provided a flat panel detector 70 that is movable bidirectionally along the Z axis as indicated by an arrow. The cradle 117 can move in the Z-axis direction on a table, and can move in the Y-axis direction.

As shown in FIGS. 3B and 3C, guide rails 77 are provided in the hollow space of the cradle 117 so that the flat panel detector 70 can smoothly move in a specific direction. The guide rails 77 are made of X-ray transparent hard plastic or the like so that the guide rails 77 do not cast the shadow on X-ray CT scanned images. The length of the guide rails 77 is equal to the length of the cradle in the Z-axis direction. Four tires 75 corresponding to the guide rails 77 are provided on the flat panel detector 70. A driving motor 73 is provided in the flat panel detector 70 to drive the tires 75. A two-dimensional panel sensor 71 is provided on an X-Z plane in the flat panel detector 70. The two-dimensional panel sensor 71 is comprised for example of a scintillator and a sensor, such as CCD sensor, MOS sensor, or CMOS sensor. When the X-ray CT scan is performed, the flat panel detector 70 has been moved to a retracted position that is at the end of the cradle 117 facing toward the +Z-axis direction. Therefore, the two-dimensional panel sensor 71, driving motor 73 and tires 75 may contain materials, such as metal, which are not completely transparent to X rays, without any problem.

A transparent window 78 made of plastic is formed in a part of a top plate of the cradle 117. This allows an operator to visually check where the flat panel detector 70 is located in actuality. The transparent window 78 may preferably be provided near a side of the top plate of the cradle 117 so that the position of the flat panel detector 70 can be checked even when the examinee's body is laid on the cradle 117 in a decubitus position. A center line is marked on the top face of the flat panel detector 70 so that the center of the two-dimensional panel sensor 71 along the length in the Z-axis direction can be seen through the transparent window 78.

In order to supply power to the two-dimensional panel sensor 71 and the driving motor 73, a power cable (not shown) is provided between the flat panel detector 70 and the cradle 117, and likewise a signal line through which a signal is output from the two-dimensional panel sensor 71 is provided between the flat panel detector 70 and the cradle 117. As shown in FIGS. 3B and 3C, the driving motor 73 is arranged in the flat panel detector 70 in this embodiment, but may alternatively be arranged in the cradle 117. Further provided in the cradle 117 is, as shown in FIG. 3C, a position sensor 79 for detecting where (in the Z-axis direction) in the cradle 117 the flat panel detector 70 is located. In an embodiment where the driving motor 73 is a stepping motor or the like, the position of the flat panel detector 70 can be detected if the position of the flat panel detector 70 is initialized every time upon startup, and thus such a position sensor 79 would not necessarily required.

<Detection of Error DF between X-Ray Tube and the Collimator Center>

This invention explains two exemplary embodiments, which detect error DF between the X-ray tube 125 and the center of a pair of the collimator 126, as a method of adjusting a plane of rotation of the X-ray tube 125.

First Exemplary Embodiment

Figure 4:
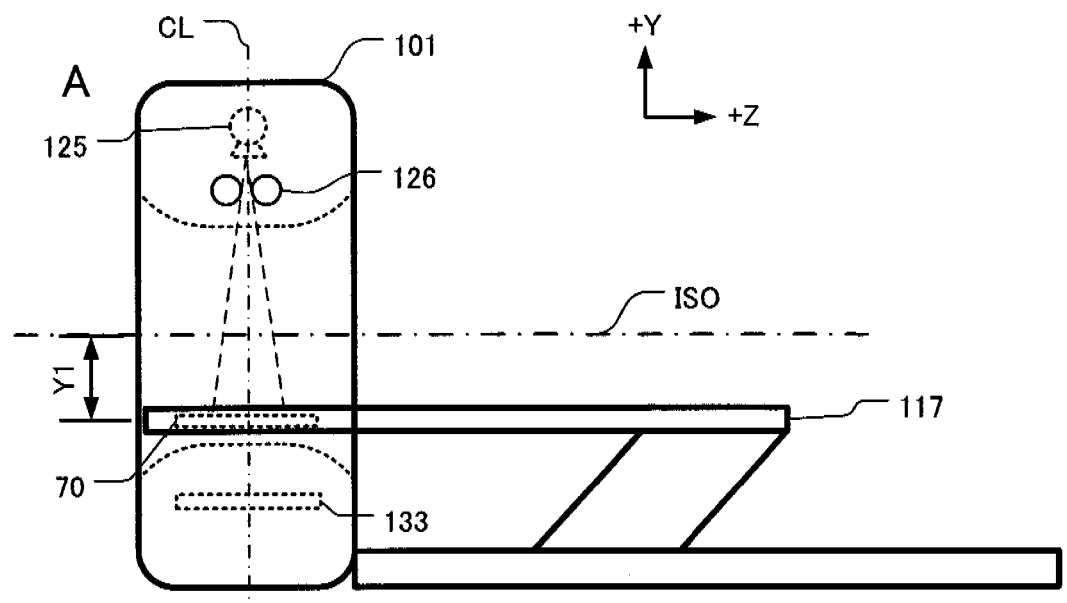
FIG. 4 is a first exemplary embodiment, where
Figure 4:
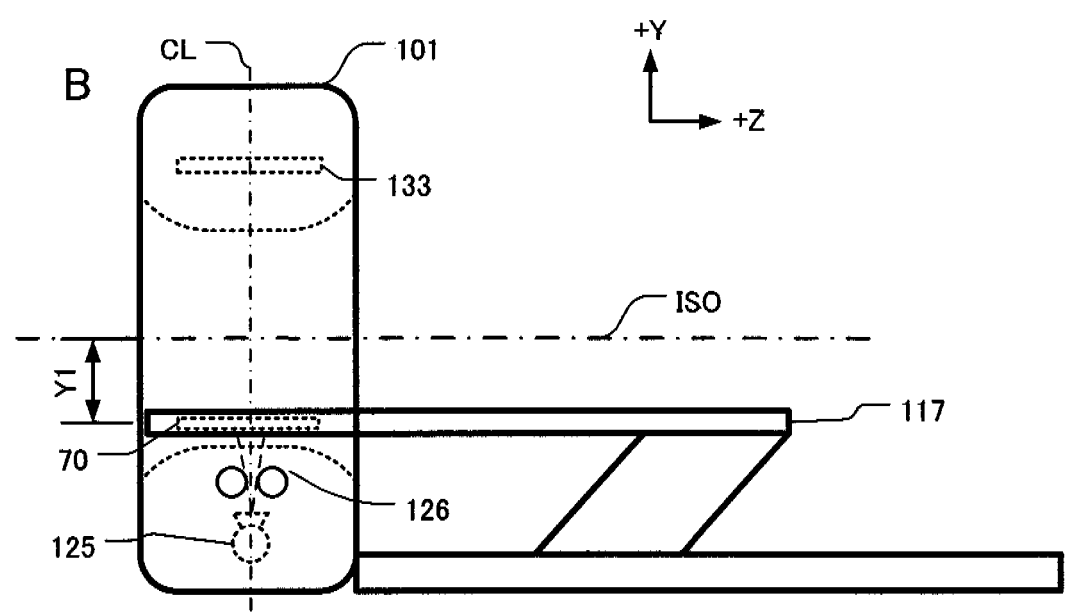

FIG. 4A is a figure irradiating X-rays from the X-ray tube 125 positioned at a position of 0 degrees, and FIG. 4B is a figure irradiating X-rays from the X-ray tube 125 positioned at a position of 180 degrees. The cradle 117 is arranged at the position that is shifted only distance Y1 in Y-axis direction from pivot line ISO. And the center of flat panel detector 70 moves to central CL of gantry 101 to detect X-rays from the X-ray tube 125.

Figure 5:
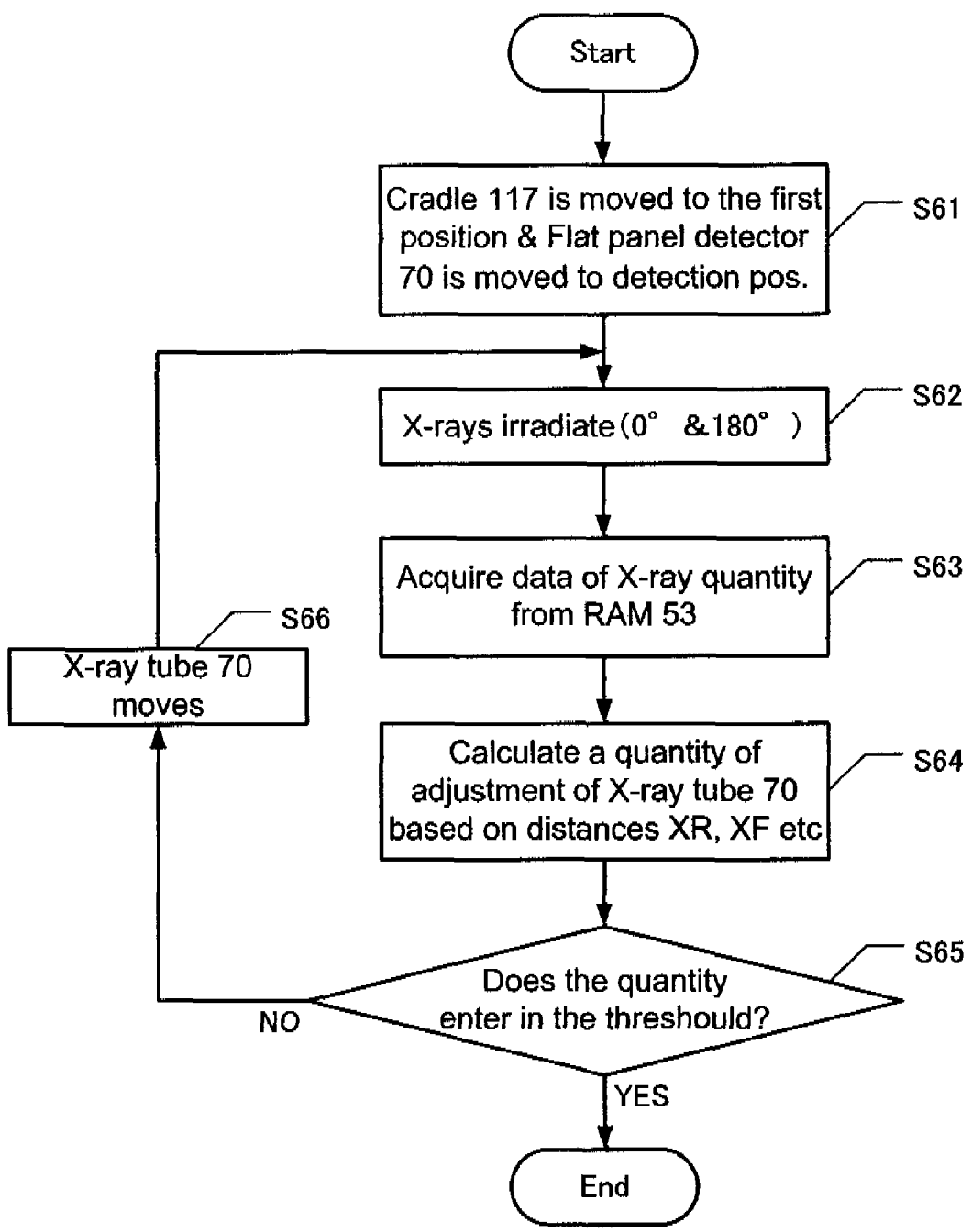
FIG. 5 is a flowchart to get error DF within the threshold according to the first exemplary embodiment.

FIG. 5 is a flowchart to get error DF within the threshold according to the first exemplary embodiment.

In step S61, the cradle 117 moves to a remote position, or the first position where distance Y1 is apart from the pivot line ISO. Furthermore, the cradle 117 moves to a hollow part of the gantry 101 so that the flat panel detector 70 can move to central CL of the gantry 101. Afterwards, the flat panel detector 70 moves to central CL of gantry 101.

In step S62, the X-ray tube 125 is positioned at a position of 0 degrees as shown in FIG. 4A. The collimator 126 is coordinated to a predetermined width so that X-rays enter in width of Z-axis direction of the flat panel detector 70. The X-ray tube 125 irradiates X-rays of predetermined amount mA. The flat panel detector 70 detects X-rays on two-dimensional surface. The detected X-rays with the two-dimensional surface position information thereof are sent to storage devices such as RAM 53 of operation console 50.

Next, the gantry rotor 130 is turned by a gantry turn motor 131, and the X-ray tube 125 is positioned at a position of 180 degrees as shown in FIG. 4B. The collimator 126 is kept as the predetermined width. Then the X-ray tube 125 irradiates X-rays of predetermined amount mA. The flat panel detector 70 detects X-rays on two-dimensional surface. The detected X-rays with the two-dimensional surface position information thereof are sent to storage devices such as RAM 53 of operation console 50. If the flat panel detector 70 can save an X-ray exposure dose temporarily, after adding X-ray quantity of when the X-ray tube 125 is positioned at a position of 180 degrees to X-ray quantity when the X-ray tube 125 was positioned at a position of 0 degrees, X-ray quantity may be send to the storage devices such as RAM 53.

In step S63, data based on X-ray quantity where the X-ray tube 125 was positioned at positions of 0 degrees and 180 degrees are acquired from RAM 53. Actually CPU 54 only calculates data, does not show an image, but, for the explanation, FIG. 6A shows an exemplary synthesized image.

In step S64, quantity of adjustment of the X-ray tube 125 is calculated on the basis of result on the distance XR, the distance XF and so on of FIG. 6A. FIG. 6B explains a concrete method of calculation.

In step S65, the CPU 54 judges whether quantity of adjustment of the X-ray tube 125 enters in the threshold or not. If the quantity of adjustment enters in the threshold, the calculation of this flowchart is finished, and if quantity of adjustment does not enter in the threshold, the step moves to step S66.

In step S66, the X-ray tube 125 is moved by manual operation based on the quantity of adjustment of the X-ray tube 125. Then, step S62 through step S66 are repeated again until the quantity of adjustment enters in the threshold. In this flowchart, plane of rotation POR is coordinated by moving the X-ray tube 125, but plane of rotation POR can be also coordinated by moving an initial position of the collimator 126.

Next, FIG. 6B explains operation of step S64.

The center line of a pair of the collimator 126 is plane of rotation POR. Distance CO is the distance between an end of one the collimator 126 and the plane of rotation POR. The detection plane is away from the pivot line ISO in Y-axis direction by distance Y1. The detection plane is a plane of a scintillator of flat panel detector 70.

The focus F of an anode irradiating X-rays of the X-ray tube 125 is away from the plane of rotation POR by an error DF. The distance FT of the X-ray tube 125 is a distance between the focus F and pivot line ISO, and the distance FC is a distance between the focus F of the X-ray tube 125 and the collimator 126. When the X-ray tube 125 is positioned at a position of 0 degrees, X-ray tube 125 is denoted by F(0°), and when the X-ray tube 125 is positioned at a position of 180 degrees, X-ray tube 125 is denoted by F(180°).

The output, as shown in FIG. 6A, is provided on the detection plane of the flat panel detector 70 when the X-ray tube 125 is positioned at a position of 0 degrees and when the X-ray tube 125 is positioned at a position of 180 degrees. In an image of the detection plane, white BB' is an range where both X-rays on F(0°) and on F(180°) were irradiated, gray XF and gray XR ranges are ranges where X-rays on F(0°) were irradiated. A black range is the range where X-rays were not irradiated.

In the case of the above-mentioned relations, the following formulas have equality, can determine an error DF.

$$XF=((CO+DF)/FC)*((FI+Y1)-(FI-Y1))$$

$$XR=((CO-DF)/FC)*((FI+Y1)-(FI-Y1))$$

$$DF=(XF-XR)*(FC/4*Y1)$$

As the error DF is determined, it is possible to adjust the plane of rotation POR to move the X-ray tube 125 by DF as the quantity of adjustment. The exemplary embodiment describes the X-ray tube 125 at a position of 0 degrees and a position of 180 degrees, however it is possible to locate X-ray tube 125 at facing positions, for example, at a position of 5 degrees and position 185 degrees like that. At the time, the degrees between the plane of the flat panel detector 70 and X-ray tube 125 should be calculated.

Second Exemplary Embodiment

Figure 7:
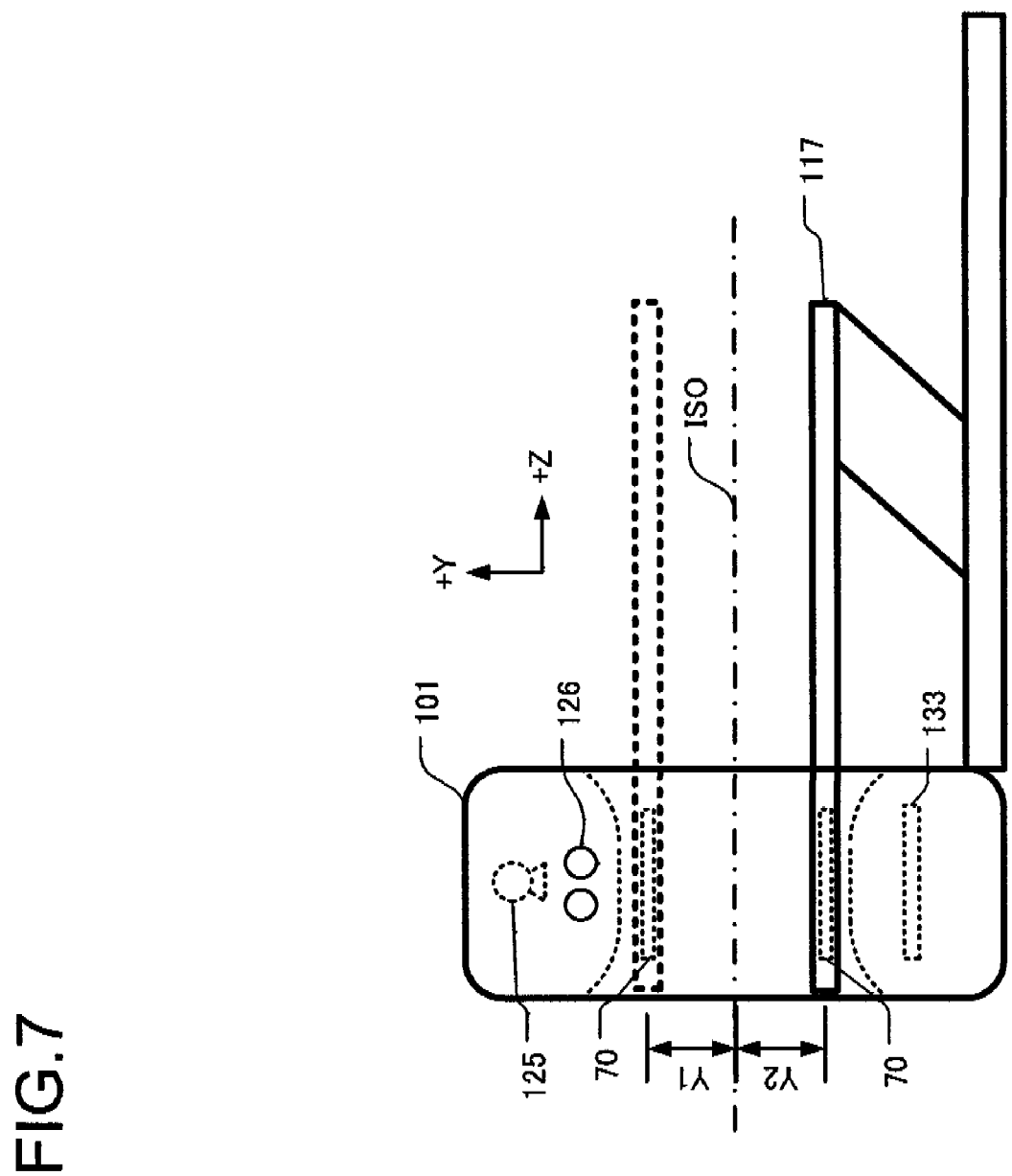
FIG. 7 is a second exemplary embodiment, which shows an X-rays irradiating from the X-ray tube 125 positioned at a position of 0 degrees.

FIG. 7 shows an X-rays irradiating from the X-ray tube 125 positioned at a position of 0 degrees, and the cradle 117 is positioned at the position in +Y axial direction from pivot line ISO by Y1 (a position shown in a dotted line) and at the position in −Y axial direction from pivot line ISO by Y2. The center of flat panel detector 70 moves to central CL of gantry 101 to detect X-rays from the X-ray tube 125.

Figure 8:
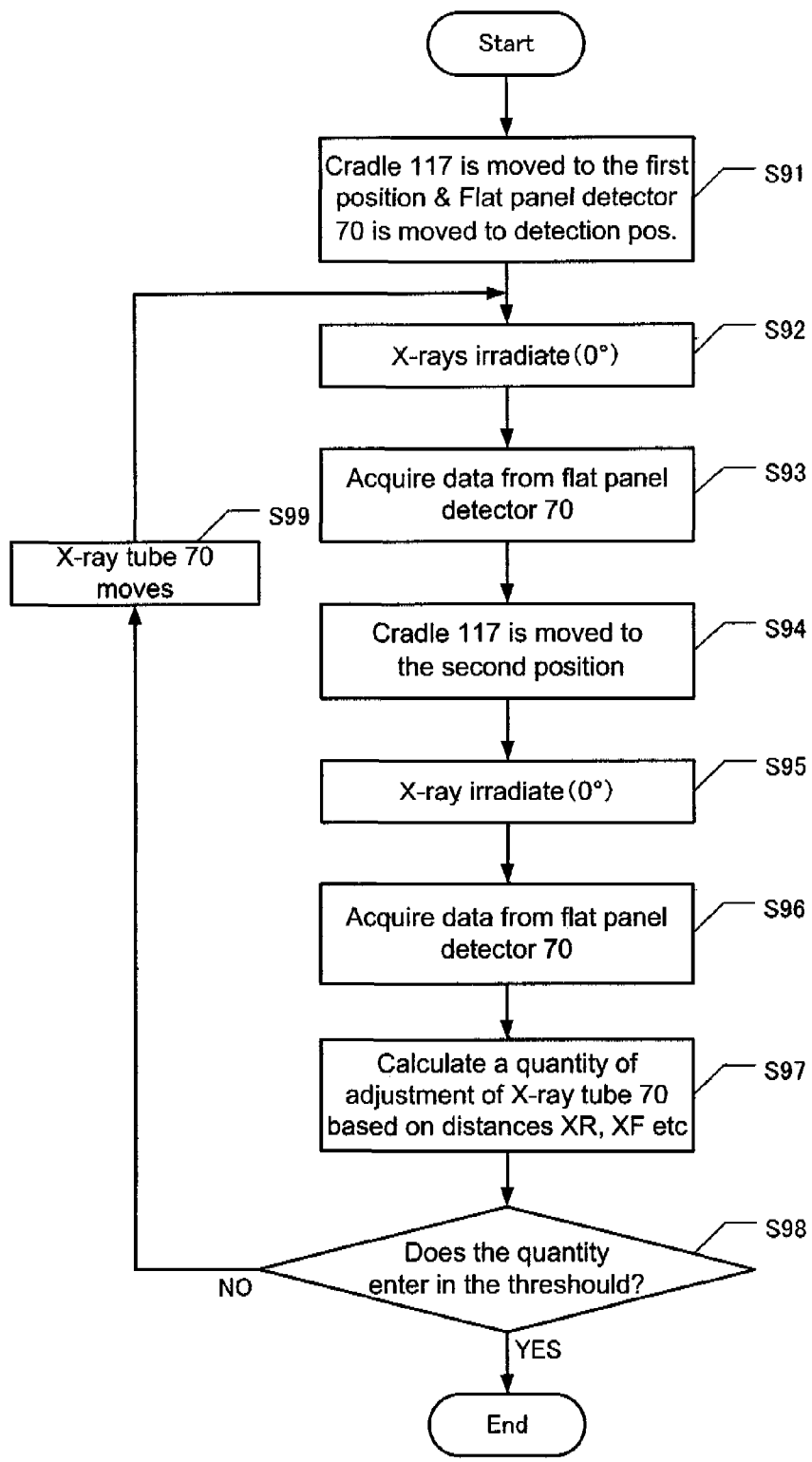
FIG. 8 is a flowchart to get error DF within the threshold according to the second exemplary embodiment.

FIG. 8 is a flowchart to get error DF within the threshold according to the second exemplary embodiment.

In step S91, the cradle 117 moves to a first position where distance Y1 is apart from the pivot line ISO. Furthermore, the cradle 117 moves to a hollow part of the gantry 101 so that the flat panel detector 70 can move to central CL of the gantry 101. Afterwards, the flat panel detector 70 moves to central CL of gantry 101.

In step S92, the X-ray tube 125 is positioned at a position of 0 degrees. The collimator 126 is coordinated to a predetermined width so that X-rays enter in width of Z-axis direction of the flat panel detector 70. The X-ray tube 125 irradiates X-rays of predetermined amount mA.

In step S93, the flat panel detector 70 detects X-rays on two-dimensional surface. The detected X-rays with the two-dimensional surface position information thereof are sent to storage devices such as RAM 53 of operation console 50.

In step S94, the cradle 117 moves to a second position where distance Y2 is apart from the pivot line ISO.

In step S95, the X-ray tube 125 positioned at a position of 0 degrees irradiates X-rays of predetermined amount mA.

In step S96, the flat panel detector 70 detects X-rays on two-dimensional surface. The detected X-rays with the two-dimensional surface position information thereof are sent to storage devices such as RAM 53 of operation console 50. If the flat panel detector 70 can save an X-ray exposure dose temporarily, after adding X-ray quantity of when the cradle 117 is positioned at the second position to X-ray quantity when the cradle 117 was positioned at the first position, X-ray quantity may be send to the storage devices such as RAM 53.

Figure 9:
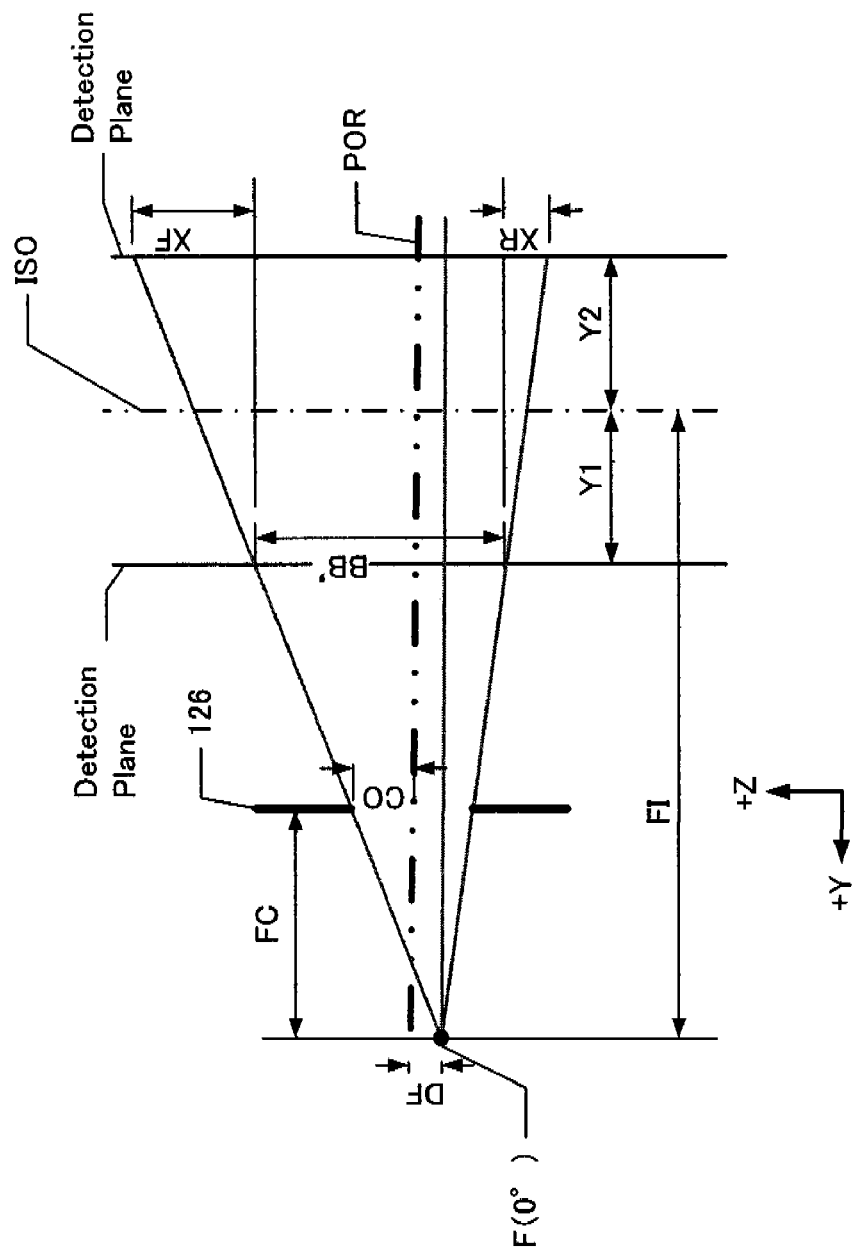
FIG. 9 is a conception diagram pursuing error DF according to the second exemplary embodiment.

In step S97, quantity of adjustment of the X-ray tube 125 is calculated on the basis of the result on the distance XR, the distance XF and so on. FIG. 9 explains a concrete method of calculation.

In step S98, the CPU 54 judges whether quantity of adjustment of the X-ray tube 125 enters in the threshold or not. If the quantity of adjustment enters in the threshold, the calculation of this flowchart is finished, and if quantity of adjustment does not enter in the threshold, the step moves to step S66.

In step S99, the X-ray tube 125 is moved by manual operation based on the quantity of adjustment of the X-ray tube 125. Then, step S92 through step S99 are repeated again until the quantity of adjustment enters in the threshold. As explained in the first exemplary embodiment, plane of rotation POR can be also coordinated by moving an initial position of the collimator 126.

FIG. 9 explains operation of step S97.

Figure 6:
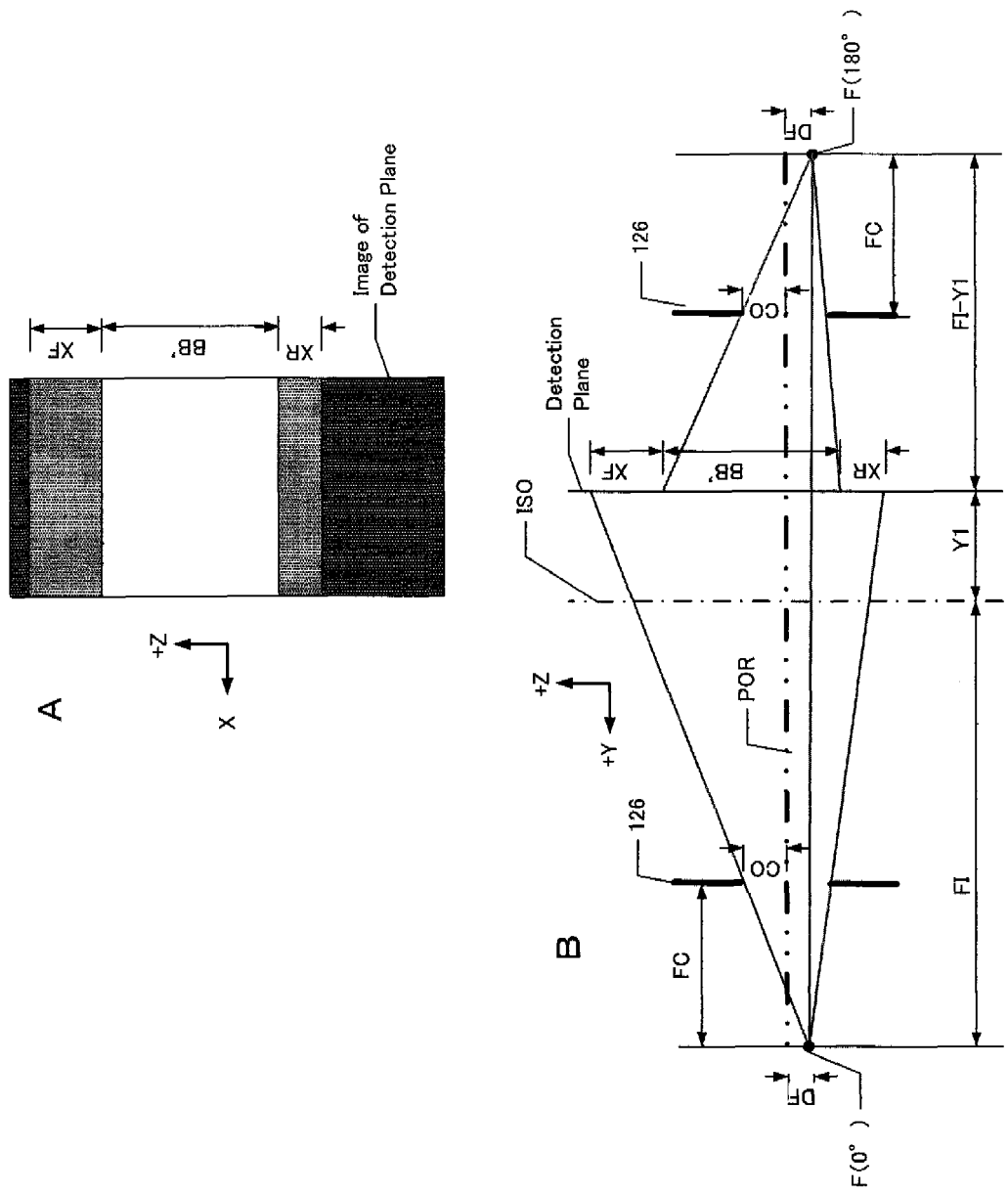
FIG. 6A shows X-ray quantity found in the flat panel detector 70.
FIG. 6B is a conception diagram pursuing error DF according to the first exemplary embodiment.

As the marks in FIG. 9 are the same as those of FIG. 6, explanation of marks is spared. However, the detection plane is positioned at distance +Y1 and distance −Y2 apart from the pivot line ISO.

When the X-ray tube 125 is positioned at the distance +Y1 and when the X-ray tube 125 is positioned at the distance −Y2, X-rays are irradiated. In an image of the detection plane, white BB' is an range where both X-rays at the distances +Y1 and −Y2 were irradiated, gray XF and gray XR ranges are ranges where X-rays at the distance −Y2 were irradiated. A black range is the range where X-rays were not irradiated.

In the case of the above-mentioned relations, the following formulas have equality, can determine an error DF.

$$XF=((CO+DF)/FC)*((FI+Y2)-(FI-Y1))$$

$$XR=((CO-DF)/FC)*((FI+Y2)-(FI-Y1))$$

$$DF=(XF-XR)*(FC/2*(Y1+Y2))$$

As the error DF is determined, it is possible to adjust the plane of rotation POR to move the X-ray tube 125 by DF as the quantity of adjustment. The exemplary embodiment describes the X-ray tube 125 at the position of 0 degrees, however, it is possible to locate X-ray tube 125 at the position of 180 degrees. Although the calculation of this flowchart becomes complicated, the X-ray tube 125 may be located at a position of 5 degrees and position 185 degrees like that.

There are various methods for detecting an edge of white BB' or a black range and ranges of gray XF or gray XR in the both first and second exemplary embodiments. For example, detection methods are Sobel Edge Detector method, Cross Edge Detector method, Canny Edge Detector method or Compass Edge Detector method.

This invention is explained by the embodiments which have the flat panel detector 70 in the cradle 117. However, this invention can apply to an X-ray CT system which does not have a flat panel detector in a cradle.

For example, a commercial flat panel detector is placed on a cradle and it is applied to the first and second exemplary embodiments. When the commercial flat panel detector doesn't move in Y-axis direction like the second exemplary embodiment, a second flat panel detector 80 showing for FIG. 10 may be prepared.

Figure 10:
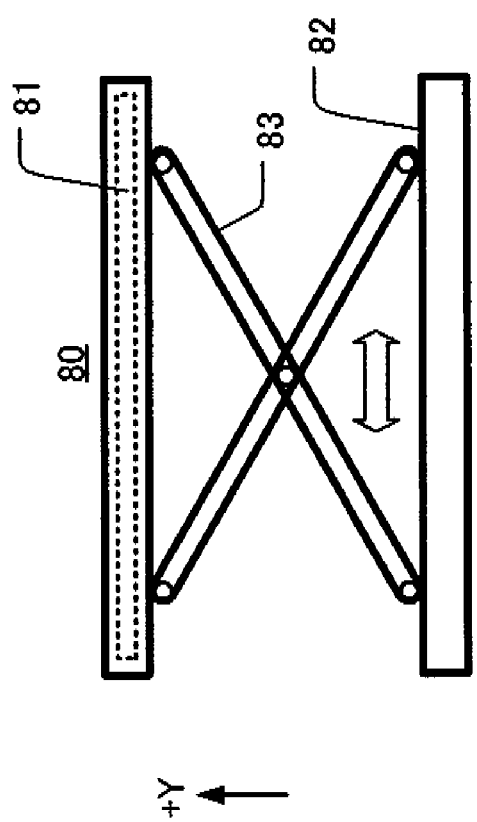
FIG. 10 shows a second flat panel detector 80.

FIG. 10 shows the second flat panel detector 80, two-dimensional panel sensor 81 can move in Y-axis direction up and down. Link bars 83 connected to two-dimensional panel sensor 81 and base 82 can move from side to side in FIG. 10. So the second exemplary embodiments can be applied by this flat panel detector 80.

In the illustrated embodiments, medical X-ray CT systems 100 have been described by way of example. However, this invention can be used in an industrial X-ray CT system or combined with any other systems; for example, X-ray CT-PET systems, and X-ray CT-SPECT systems.

What is claimed is:

1. An X-ray radiography apparatus having an X-ray tube, an X-ray detector opposing the X-ray tube for detecting irradiated X-rays from the X-ray tube, and a collimator having an opening which limits a range of X-rays irradiated to the X-ray detector, the X-ray radiography apparatus comprising:

an X-ray detector for the X-ray tube position inspection, which detects the X-rays through the collimator from the X-ray tube at two or more different distances from the X-ray tube;

calculation means for calculating a position error of the X-ray tube using a difference of a respective X-ray detection position from a plane of rotation detected at the two or more different distances; and adjusting means for adjusting a position of the X-ray tube based on the position error of the X-ray tube calculated by the calculation means.

2. The X-ray radiography apparatus according to claim 1, wherein the X-ray detector for the X-ray tube position inspection detects X-rays through the collimator from the X-ray tube at two or more different distances respectively by placing the X-ray tube 180 degrees opposite across the X-ray detector for the X-ray tube position inspection.

3. The X-ray radiography apparatus according to claim 1, wherein the X-ray detector for the X-ray tube position inspection detects X-rays through the collimator from the X-ray tube at two or more different distances respectively by moving the X-ray detector for the X-ray tube position inspection to the X-ray tube.

4. The X-ray radiography apparatus according to claim 1, wherein the X-ray radiography apparatus having:
   an X-ray CT unit for obtaining a tomography images of an examinee's body, providing a first X-ray tube, a first X-ray detector, placed the first X-ray tube opposite, for detecting irradiated X-rays from the first X-ray tube, rotor means for rotating around the examinee's body with maintaining position relations among the first the X-ray tube and the first X-ray detector, and a collimator having an opening limiting an X-ray range irradiated to the first X-ray detector;
   an X-ray CR unit for obtaining radiographic images of the examinee's body, providing a second X-ray tube, and a second X-ray detector, placed the second X-ray tube opposite across the examinee's body, for detecting irradiated X-rays from the second X-ray tube; wherein
   the X-ray tube which the position error is the first the X-ray tube;
   the X-ray detector for the X-ray tube position inspection is the second X-ray detector; and
   the adjusting means adjusts position error of the plane of rotation by rotor means of the X-ray CT unit.

5. The X-ray radiography apparatus according to claim 1, wherein the X-ray detector for the X-ray tube position inspection is located inside a cradle laying the examinee's body.

6. An adjustment method for adjusting a position of a plane of rotation defined by a collimator and an X-ray tube of an X-ray radiography apparatus, the method comprising:
   detecting a range of first X-rays from the X-ray tube positioned at a first position with an X-ray detector;
   moving the X-ray tube from the first position to a second position which is different from the first position;
   detecting a range of second X-rays from the X-ray tube positioned at the second position with the X-ray detector; and
   calculating a quantity of adjustment of the X-ray tube and the collimator based on a detected position of the plane of rotation from the detected ranges of the first X-rays and of the second X-rays.

7. The adjustment method for adjusting a position of a plane of rotation according to claim 6, wherein the first position and the second position are placed 180 degrees opposite across the X-ray detector.

8. The adjustment method for adjusting a position of a plane of rotation according to claim 7, wherein the step of calculating quantity of adjustment calculates the quantity of adjustment by calculating the detected range width only by the second X-rays.

9. The adjustment method for adjusting a position of a plane of rotation according to claim 6, further comprising:
   positioning an X-ray detector at a third position in an X-ray irradiation direction from the X-ray tube;
   detecting a range of third X-rays from the X-ray tube with an X-ray detector positioned at the third position;
   moving the X-ray detector to a fourth position in an irradiation direction that is different from the third position;
   detecting a range of fourth X-rays from the X-ray tube with an X-ray detector positioned at the fourth position; and
   calculating the quantity of adjustment of the X-ray tube and the collimator based on the detected ranges of the third X-rays and of the fourth X-rays.

10. The adjustment method for adjusting a position of a plane of rotation according to claim 6, wherein the X-ray detector is located inside a cradle laying the examinee's body.

11. The adjustment method for adjusting a position of a plane of rotation according to claim 9, wherein the step of calculating quantity of adjustment calculates the quantity of adjustment by calculating detected range width only of the four X-rays.

12. The adjustment method for adjusting a position of a plane of rotation according to claim 6, further comprising a step of moving the X-ray tube based on the quantity of the adjustment.

13. The adjustment method for adjusting a position of a plane of rotation according to claim 6, wherein, the adjustment method of the plane of rotation is performed when the X-ray tube is installed first or when the X-ray tube is replaced.

14. The X-ray radiography apparatus according to claim 2, wherein the X-ray radiography apparatus having:
   an X-ray CT unit for obtaining a tomography images of an examinee's body, providing a first X-ray tube, a first X-ray detector, placed the first X-ray tube opposite, for detecting irradiated X-rays from the first X-ray tube, rotor means for rotating around the examinee's body with maintaining position relations among the first the X-ray tube and the first X-ray detector, and a collimator having an opening limiting an X-ray range irradiated to the first X-ray detector;
   an X-ray CR unit for obtaining radiographic images of the examinee's body, providing a second X-ray tube, and a second X-ray detector, placed the second X-ray tube opposite across the examinee's body, for detecting irradiated X-rays from the second X-ray tube; wherein
   the X-ray tube which the position error is the first the X-ray tube;
   the X-ray detector for the X-ray tube position inspection is the second X-ray detector; and
   the adjusting means adjusts position error of the plane of rotation by rotor means of the X-ray CT unit.

15. The X-ray radiography apparatus according to claim 3, wherein the X-ray radiography apparatus having:
   an X-ray CT unit for obtaining a tomography images of an examinee's body, providing a first X-ray tube, a first X-ray detector, placed the first X-ray tube opposite, for detecting irradiated X-rays from the first X-ray tube, rotor means for rotating around the examinee's body with maintaining position relations among the first the X-ray tube and the first X-ray detector, and a collimator having an opening limiting an X-ray range irradiated to the first X-ray detector;
   an X-ray CR unit for obtaining radiographic images of the examinee's body, providing a second X-ray tube, and a second X-ray detector, placed the second X-ray tube opposite across the examinee's body, for detecting irradiated X-rays from the second X-ray tube; wherein
   the X-ray tube which the position error is the first the X-ray tube;
   the X-ray detector for the X-ray tube position inspection is the second X-ray detector; and
   the adjusting means adjusts position error of the plane of rotation by rotor means of the X-ray CT unit.

16. The adjustment method for adjusting a position of a plane of rotation according to claim 9, wherein the X-ray detector is located inside a cradle laying the examinee's body.

17. The adjustment method for adjusting a position of a plane of rotation according to claim 9, further comprising a step of moving the X-ray tube based on the quantity of the adjustment.

18. The adjustment method for adjusting a position of a plane of rotation according to claim 9, wherein, the adjustment method of the plane of rotation is performed when the X-ray tube is installed first or when the X-ray tube is replaced.

* * * * *